(12) United States Patent
Kunz et al.

(10) Patent No.: US 10,912,572 B2
(45) Date of Patent: Feb. 9, 2021

(54) DENTAL DRILL BIT

(71) Applicant: Nobel Biocare Services AG, Kloten (CH)

(72) Inventors: Pascal Kunz, Zürich-Flughafen (CH); Ulf Johansson, Kungälv (SE)

(73) Assignee: Nobel Biocare Services AG, Kloten (CH)

(*) Notice: Subject to any disclaimer, the term of this patent is extended or adjusted under 35 U.S.C. 154(b) by 533 days.

(21) Appl. No.: 14/759,920

(22) PCT Filed: Jan. 9, 2014

(86) PCT No.: PCT/EP2014/000025
§ 371 (c)(1),
(2) Date: Jul. 8, 2015

(87) PCT Pub. No.: WO2014/108332
PCT Pub. Date: Jul. 17, 2014

(65) Prior Publication Data
US 2015/0342617 A1 Dec. 3, 2015

(30) Foreign Application Priority Data
Jan. 11, 2013 (GB) .................... 1300486.6

(51) Int. Cl.
*A61C 1/14* (2006.01)
*A61C 3/02* (2006.01)
(Continued)

(52) U.S. Cl.
CPC .......... *A61B 17/1615* (2013.01); *A61C 1/084* (2013.01); *A61C 1/14* (2013.01); *A61C 3/02* (2013.01); *A61C 8/0089* (2013.01)

(58) Field of Classification Search
CPC .......... A61C 1/082; A61C 1/084; A61C 1/14; A61C 3/02; A61C 8/0089
See application file for complete search history.

(56) References Cited

U.S. PATENT DOCUMENTS

| 4,246,811 A | 1/1981 | Bondhus |
| 4,345,899 A | 8/1982 | Vlock |

(Continued)

FOREIGN PATENT DOCUMENTS

| DE | 10 2009 015358 A1 | 9/2010 |
| EP | 0 997 111 A2 | 5/2000 |

(Continued)

OTHER PUBLICATIONS

International Search Report for Application No. PCT/EP2014/000025 dated Apr. 3, 2014 in 6 pages [the ISR for the PCT Application of this US national phase application].

*Primary Examiner* — Heidi M Eide
*Assistant Examiner* — Drew S Folgmann
(74) *Attorney, Agent, or Firm* — Knobbe, Martens, Olson & Bear, LLP

(57) ABSTRACT

A dental drill bit is combined with a surgical template provided with a guide hole adapted to guide the dental drill bit directly or via a guide sleeve provided in the guide hole. The dental drill bit has a first end, a second end, a spherical drill head arranged at the first end, and at least one helical flute extending from the spherical drill head towards the second end. The portion of the dental drill bit having the at least one helical flute is substantially cylindrical. A use of such a dental drill bit and a method of drilling a hole in an oblique bone surface of a jaw bone of a patient are also provided.

9 Claims, 3 Drawing Sheets

(51) Int. Cl.
*A61B 17/16* (2006.01)
*A61C 8/00* (2006.01)
*A61C 1/08* (2006.01)

(56) References Cited

U.S. PATENT DOCUMENTS

| | | | |
|---|---|---|---|
| 4,384,812 A | 5/1983 | Miyagawa | |
| 4,459,074 A | 7/1984 | Capuano | |
| 5,284,073 A | 2/1994 | Wright et al. | |
| 5,320,529 A | 6/1994 | Pompa | |
| 5,362,236 A | 11/1994 | Branemark | |
| 5,370,021 A | 12/1994 | Shigematsu | |
| 5,564,926 A | 10/1996 | Branemark | |
| 5,573,401 A | 11/1996 | Davidson et al. | |
| 5,575,650 A | 11/1996 | Niznick et al. | |
| 5,685,671 A * | 11/1997 | Packer | B23C 5/1018 407/118 |
| 5,743,916 A | 4/1998 | Greenberg et al. | |
| 5,752,828 A | 5/1998 | Andersson et al. | |
| 5,772,437 A | 6/1998 | Rangert et al. | |
| 5,868,049 A | 2/1999 | Kanwal | |
| 5,967,777 A | 10/1999 | Klein et al. | |
| 5,989,025 A | 11/1999 | Conley | |
| 6,036,410 A | 3/2000 | Shun'ko | |
| 6,053,920 A | 4/2000 | Carlsson et al. | |
| 6,106,291 A * | 8/2000 | Boston | A61C 3/02 433/165 |
| 6,319,610 B1 | 11/2001 | Zimmer | |
| 6,402,449 B1 | 6/2002 | Lin | |
| 6,561,805 B2 | 5/2003 | Kumar | |
| 6,626,911 B1 | 9/2003 | Engman et al. | |
| 6,641,395 B2 | 11/2003 | Kumar et al. | |
| 6,733,291 B1 | 5/2004 | Hurson | |
| 6,913,465 B2 | 7/2005 | Howlett et al. | |
| 6,955,258 B2 | 10/2005 | Howlett et al. | |
| 7,232,311 B1 * | 6/2007 | Greggs | A61C 3/02 433/165 |
| 7,559,765 B2 * | 7/2009 | Courvoisier | A61B 17/16 408/224 |
| 7,665,989 B2 | 2/2010 | Brajnovic et al. | |
| 7,846,357 B2 | 12/2010 | Johansson | |
| 7,942,668 B2 | 5/2011 | Brajnovic et al. | |
| 8,640,328 B1 | 2/2014 | Yow et al. | |
| 8,657,537 B2 * | 2/2014 | Delacretaz | A61C 3/02 407/54 |
| 9,095,377 B2 | 8/2015 | Karlsson et al. | |
| 2005/0170311 A1 | 8/2005 | Tardieu et al. | |
| 2005/0214714 A1 | 9/2005 | Wohrle | |
| 2005/0277090 A1 | 12/2005 | Anderson et al. | |
| 2006/0149264 A1 | 7/2006 | Castaneda et al. | |
| 2007/0005070 A1 | 1/2007 | Kay | |
| 2007/0248935 A1 | 10/2007 | Danger et al. | |
| 2008/0050698 A1 | 2/2008 | Carter | |
| 2008/0261176 A1 | 10/2008 | Hurson | |
| 2009/0053674 A1 | 2/2009 | Danger | |
| 2009/0202962 A1 | 8/2009 | Xam-Mar Mangrane | |
| 2009/0267251 A1 | 10/2009 | Johansson | |
| 2009/0325122 A1 | 12/2009 | Brajnovic et al. | |
| 2010/0009314 A1 | 1/2010 | Tardieu et al. | |
| 2010/0062389 A1 * | 3/2010 | Drews | A61B 17/176 433/75 |
| 2010/0112517 A1 | 5/2010 | Chen | |
| 2010/0167240 A1 | 7/2010 | Benzon et al. | |
| 2010/0285427 A1 | 11/2010 | Hung | |
| 2010/0291509 A1 | 11/2010 | Berggren et al. | |
| 2010/0312248 A1 | 12/2010 | Karlsson et al. | |
| 2011/0229853 A1 | 9/2011 | Chen | |
| 2012/0135373 A1 * | 5/2012 | Cheng | A61C 1/084 433/75 |
| 2013/0006248 A1 * | 1/2013 | Ellis | A61B 17/1615 606/80 |
| 2014/0178836 A1 | 6/2014 | Haus et al. | |
| 2014/0186797 A1 | 7/2014 | Haus | |
| 2015/0238289 A1 | 8/2015 | Wouters et al. | |
| 2015/0238290 A1 | 8/2015 | Wouters et al. | |
| 2015/0245890 A1 | 9/2015 | Wouters et al. | |

FOREIGN PATENT DOCUMENTS

| | | |
|---|---|---|
| EP | 1039151 | 9/2000 |
| EP | 1 323 394 A1 | 7/2003 |
| EP | 1 712 194 A1 | 10/2006 |
| EP | 2 174 616 A1 | 4/2010 |
| GB | 191417073 | 2/1916 |
| GB | 575978 | 4/1944 |
| GB | 2 154 487 A | 9/1985 |
| JP | 2007-520295 | 7/2007 |
| WO | WO 00/27300 | 5/2000 |
| WO | WO 2003/003937 | 1/2003 |
| WO | WO 2005/030081 A1 | 4/2005 |
| WO | WO 2008/064350 | 5/2008 |
| WO | WO 2010/054169 A1 | 5/2010 |
| WO | WO 2011/023750 A2 | 3/2011 |
| WO | WO 2013/004386 | 1/2013 |
| WO | WO 2014/095033 | 6/2014 |
| WO | WO 2014/095034 | 6/2014 |

* cited by examiner

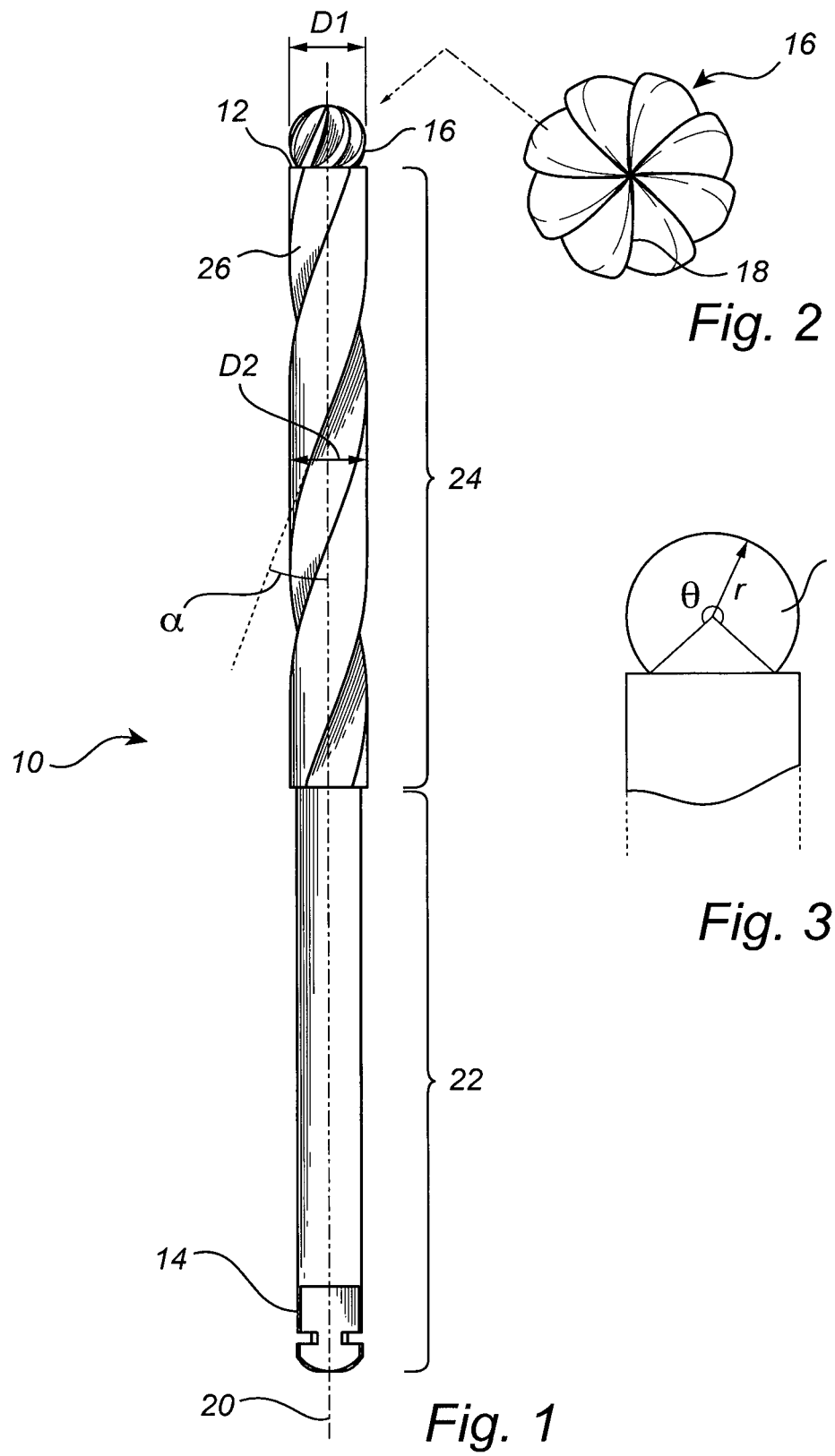

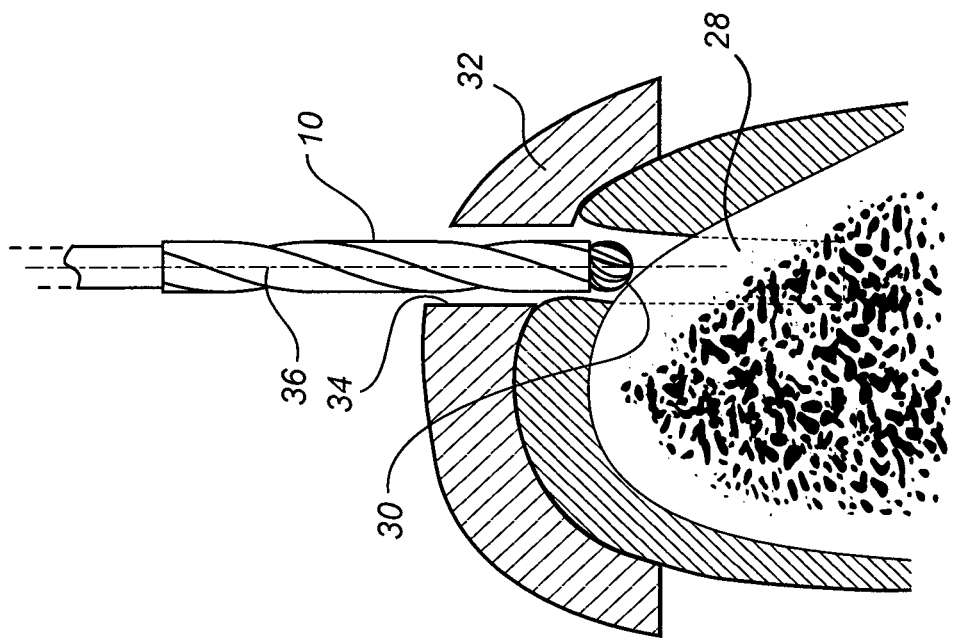
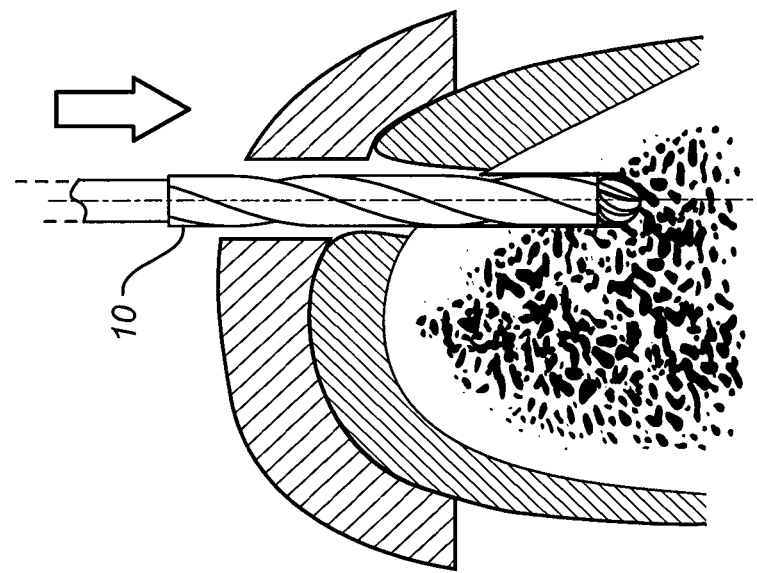

DENTAL DRILL BIT

CROSS-REFERENCE TO RELATED APPLICATIONS

This application is a national stage application under 35 U.S.C. § 371 of International Application No. PCT/EP2014/000025, filed on Jan. 9, 2014, which published in English as WO 2014/108332 A1 on Jul. 17, 2014 and which claims priority benefit of GB Patent Application No. 1300486.6 filed on Jan. 11, 2013.

The present invention relates to a dental drill bit. The present invention also relates to the use of such a dental drill bit. The present invention also relates to a method of drilling a hole in an oblique bone surface of a jaw bone of a patient.

A known drill bit for drilling a hole in the jaw bone of a patient comprises a cutting point at the tip of a cylindrical shaft with helical flutes. The cutting point has two straight cutting edges defining a point angle. Such a drill can be used in guided dental surgery ('Guided Twist Drill'). However, such a drill bit is not that suitable for drilling a hole in an object or surface which is very oblique in relation to the longitudinal axis of the drill bit.

Another example of a known dental drill bit is the 'Guide Drill' provided by Nobel Biocare. The 'Guide Drill' comprises a spherical drill head. The Guide Drill may be used for freehand surgery.

The present invention is defined in the appended independent claims. Embodiments are defined in the appended dependent claims.

According to an aspect of the present invention, there is provided a dental drill bit in combination with a surgical template provided with a guide hole adapted to guide the dental drill bit directly or via a guide sleeve provided in the guide hole, the dental drill bit comprising a first end, a second end, a spherical drill head arranged at the first end, and at least one helical flute extending from the spherical drill head towards the second end. The portion of the dental drill bit having the at least one helical flute may be substantially cylindrical, to fit in the guide hole/guide sleeve of the surgical template.

The spherical drill head may comprise a plurality of cutting edges.

The spherical drill head may be radially centralized.

The dental drill bit may further comprise a longitudinal axis extending through the first end and the second end, wherein the longitudinal axis lies in a plane in which the spherical drill head defines a circle sector having a sector angle equal to or greater than 180 deg.

A portion of the dental drill bit at the second end may be adapted for attachment to a drilling machine.

The at least one helical flute may have a pitch in the range of 3-20 deg.

The at least one helical flute may consist of two entwined helical flutes.

The maximum diameter of the spherical drill tip may be equal or substantially equal to the diameter of the portion of the dental drill bit having the at least one helical flute.

Another aspect of the present invention relates to the use of the dental drill bit according defined above for guided surgery, especially for drilling a hole in an object or surface which is oblique with respect to the longitudinal axis of the dental drill bit.

According to yet another aspect of the present invention, there is provided a method of drilling a hole in an oblique bone surface of a jaw bone of a patient, which method comprises: placing a surgical template with a guide hole over the oblique bone surface of the jaw bone, whereby said surface is oblique with respect to the longitudinal axis of the guide hole; inserting a dental drill bit as defined above through the guide hole; and drilling the hole in the oblique surface using the dental drill bit while the dental drill bit is guided by the guide hole or by a guide sleeve provided in the guide hole. This aspect may exhibit the same or similar technical effects and features as the previously defined aspects, and vice versa.

These and other aspects of the present invention will now be described in more detail, with reference to the appended drawings showing a currently preferred embodiment of the invention.

FIG. 1 is a side view of a dental drill bit according to an embodiment of the present invention.

FIG. 2 is a front view of the dental drill bit of FIG. 1.

FIG. 3 is a schematic side view of the drill head of the dental drill bit of FIG. 1

Figure 4:
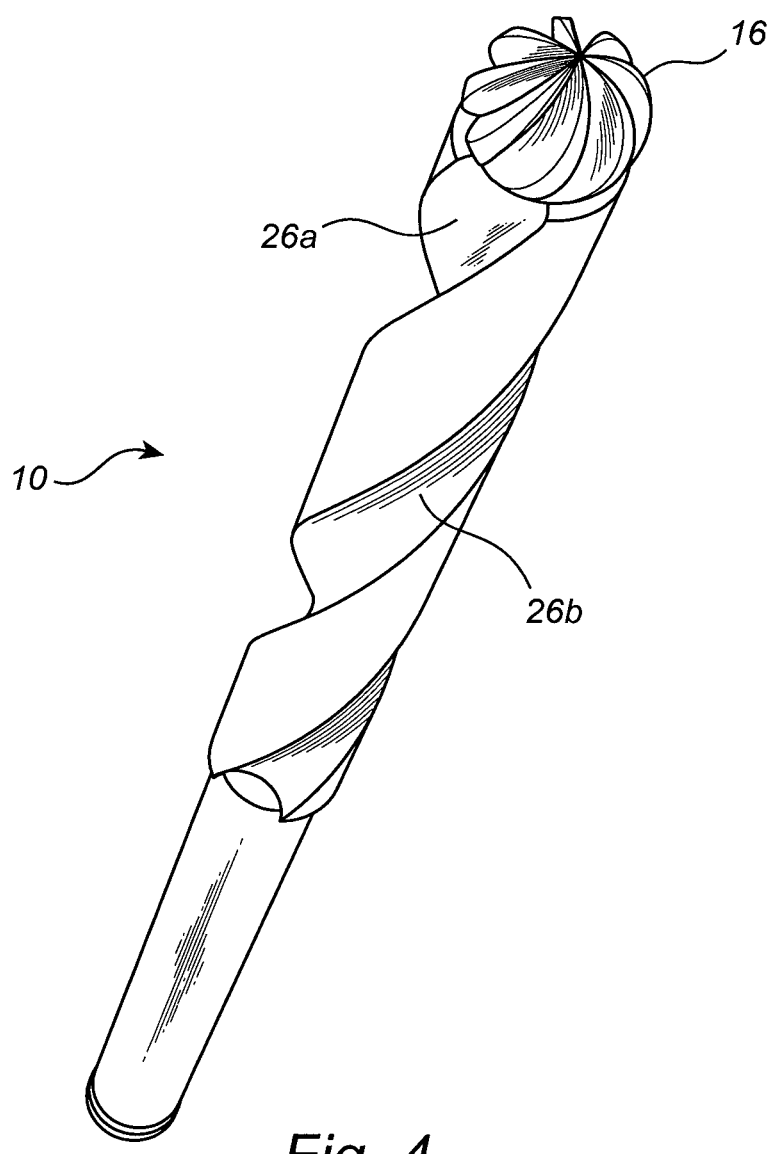
FIG. 4 is a perspective view of the drill bit of FIG. 1.

FIGS. 5*a-b* are side views showing the drill bit of FIGS. 1-4 for drilling a hole in an oblique surface using guided surgery.

FIGS. 1-4 show a dental drill bit 10 according to an embodiment of the present invention. The dental drill bit 10 is substantially straight. The dental drill bit 10 comprises a first end 12 and a second, opposite end 14. The dental drill bit 10 further comprises one spherical drill head 16 at the first end 12. The shape (radius) of the spherical drill head 16 can be completely uniform, but alternatively the radius r of the spherical drill head 16 can differ ±10%. The spherical drill head 16 comprises a plurality of cutting edges 18. Preferably, the number of cutting edges 18 is in the range of 5-8. Also preferably, the cutting edges 18 are curved. The spherical drill head 16 with the cutting edges 18 is "side cutting", which means that the present drill bit 10 can be used to drill a hole or bore in an oblique surface. Also, the spherical drill head 16 is radially centralized, which means that it is co-axial with the (central) longitudinal axis 20 extending through the first end 12 and the second end 14 of the dental drill bit 10. Also, a seen in a plane in which said longitudinal axis 20 lies, e.g. the plane of FIG. 3, the spherical drill head 16 defines a circle sector having a sector angle θ which preferably is equal to or greater than 180°. The sector angle θ may for instance be in the range of about 180°-220°. The spherical drill head 16 may substantially be of the same type as the spherical drill head of the 'Guide Drill' provided by Nobel Biocare.

At the second end 14 of the dental drill bit 10, opposite the spherical drill head 16, there is an end portion 22 which is adapted for attachment to a drilling machine (not shown). The end portion 22 may for instance be completely cylindrical, or comprise some other kind of drilling machine interface.

Between the spherical drill head 16 and the end portion 22, the dental drill bit 10 comprises an intermediate portion 24. In other words, the intermediate portion 24 extends from the spherical drill head 16 to the end portion 22. The intermediate portion 24 may be generally cylindrical throughout its length, with a constant (maximum) diameter D2 as in the illustrated embodiment. The intermediate portion 24 is provided with at least one helical or spiralling flute 26. The at least one helical flute 26 extends from the spherical drill head 16 and towards the second end 14 of the dental drill bit 10, to the end portion 22. The at least one helical flute 26 may allow passage of chips and the admission of cutting fluid (e.g. for cooling). Also, the at least one helical flute 26 can have a relatively low pitch (helix angle)

a in the range of 3°-20° with respect to the longitudinal axis 20. Preferably, the number of helical flutes is two, as in the illustrated embodiment showing a first flute 26a and second flute 26b. The flutes 26a and 26b are "entwined". Namely, they are arranged on opposite sides of the longitudinal axis 20, and they have substantially the same extents along the longitudinal axis 20.

Preferably, the maximum diameter D1 of the spherical drill tip 16 is equal or substantially equal to the diameter D2 of the intermediate portion 24, in order to create a tight distance between the drilled hole and the intermediate portion 24 to ensure that bone chips are "pumped" through the flute(s) 26 out from the drill hole. The diameters D1 and D2 may for example be in the range of 1.5-6.0 mm. Also, the intermediate portion 24 may be slightly tapered (not shown). In this case, the diameter of the intermediate portion 24 just next to the spherical drill tip 16 equals D1, and then the diameter of the intermediate portion 24 increases towards the end portion 22.

The present drill bit 10 may be used in various dental applications, such as guided surgery. However, the drill bit 10 could also be used in non-dental application.

In an exemplary method of drilling a hole 28 in an oblique bone surface 30 of a jaw bone of a patient (see FIGS. 5a-b), a surgical template 32 with a guide hole 34 is placed over the bone surface 30, whereby said surface is oblique with respect to the longitudinal axis 36 of the guide hole 34. The dental drill bit 10 is then inserted through the guide hole 34, and the hole 34 is drilled using the dental drill bit 10 being guided by the guide hole 34, or by a guide sleeve (not shown) provided in the guide hole 34. Because of the side cutting capability of the spherical drill head 16, the drill bit 10 will properly engage the oblique bone surface 30 and not "slide" sideways on the oblique bone surface 30. The latter could otherwise cause the surgical template 32 to be dislocated, which in turn could result in that the hole is not properly drilled (it could for instance have an angle deviating from the planned angle). Bone rests resulting from the drilling may be transported away by means of the helical flute(s) 26.

The person skilled in the art realizes that the present invention by no means is limited to the preferred embodiments described above. On the contrary, many modifications and variations are possible within the scope of the appended claims.

The invention claimed is:

1. A combination of a dental drill bit and a surgical template provided with a guide hole adapted to guide the dental drill bit directly or via a guide sleeve provided in the guide hole, the dental drill bit comprising a first end, a second end, a spherical drill head arranged at the first end, and at least one helical flute extending from the spherical drill head towards the second end, wherein the portion of the dental drill bit having the at least one helical flute is substantially cylindrical and configured to be guided by the guide hole or by the guide sleeve, wherein the dental drill bit further comprises a longitudinal axis extending through the first end and the second end, wherein the longitudinal axis lies in a plane in which the spherical drill head defines a circle sector having a sector angle greater than 180 degrees, and wherein only the spherical drill head comprises a plurality of cutting edges.

2. The combination according to claim 1, wherein the spherical drill head is radially centralized.

3. The combination according to claim 1, wherein a portion of the dental drill bit at the second end is adapted for attachment to a drilling machine.

4. The combination according to claim 1, wherein the at least one helical flute has a pitch in the range of 3-20 degrees.

5. The combination according to claim 1, wherein the at least one helical flute comprises two entwined helical flutes.

6. The combination according to claim 1, wherein the maximum diameter of the spherical drill head is equal or substantially equal to the diameter of the portion of the dental drill bit having the at least one helical flute.

7. A method of using the combination according to claim 1 for guided surgery, the method comprising drilling a hole in an object or surface using the dental drill bit while the dental drill bit is guided by the guide hole or by the guide sleeve provided in the guide hole.

8. The method of using the combination according to claim 7, wherein drilling a hole in an object or surface comprises drilling a hole in an object or surface which is oblique with respect to the longitudinal axis of the dental drill bit.

9. A method of drilling a hole in an oblique bone surface of a jaw bone of a patient, the method comprising:
    placing the surgical template with the guide hole of the combination according to claim 1 over the oblique bone surface of the jaw bone, wherein said surface is oblique with respect to the longitudinal axis of the guide hole;
    inserting the dental drill bit of the combination according to claim 1 through the guide hole; and
    drilling the hole in the oblique surface using the dental drill bit while the dental drill bit is guided by the guide hole or by the guide sleeve provided in the guide hole.

* * * * *